United States Patent
Chen et al.

(10) Patent No.: US 11,583,566 B2
(45) Date of Patent: Feb. 21, 2023

(54) **USE OF *SCHIZOCHYTRIUM LIMACINUM* AND ITS PREPARATION IN IMPROVING THE QUALITY AND YIELD OF ANIMAL PRODUCT**

(71) Applicant: XIAMEN HUISON BIOTECH CO., LTD, Fujian (CN)

(72) Inventors: Liyi Chen, Fujian (CN); Huichang Zhong, Fujian (CN); Shuirong Chen, Fujian (CN)

(73) Assignee: XIAMEN HUISON BIOTECH CO., LTD, Fujian (CN)

( * ) Notice: Subject to any disclaimer, the term of this patent is extended or adjusted under 35 U.S.C. 154(b) by 33 days.

(21) Appl. No.: 17/043,468

(22) PCT Filed: Nov. 14, 2018

(86) PCT No.: PCT/CN2018/115327
§ 371 (c)(1),
(2) Date: Sep. 29, 2020

(87) PCT Pub. No.: WO2019/192182
PCT Pub. Date: Oct. 10, 2019

(65) Prior Publication Data
US 2021/0205385 A1     Jul. 8, 2021

(30) Foreign Application Priority Data

Apr. 4, 2018 (CN) .......................... 201810297773.9
Apr. 4, 2018 (CN) .......................... 201810300872.8
Apr. 4, 2018 (CN) .......................... 201810300876.6

(51) Int. Cl.
| | | |
|---|---|---|
| A61K 36/02 | (2006.01) | |
| A23K 50/10 | (2016.01) | |
| A23K 50/75 | (2016.01) | |
| A23K 10/16 | (2016.01) | |
| C12N 1/12 | (2006.01) | |
| A61K 9/00 | (2006.01) | |
| C12R 1/89 | (2006.01) | |

(52) U.S. Cl.
CPC .............. *A61K 36/02* (2013.01); *A23K 10/16* (2016.05); *A23K 50/10* (2016.05); *A23K 50/75* (2016.05); *A61K 9/0056* (2013.01); *C12N 1/12* (2013.01); *C12N 1/125* (2021.05); *C12R 2001/89* (2021.05)

(58) Field of Classification Search
CPC ........ A61K 36/02; A23K 10/16; A23K 50/10; A23K 50/75; A23K 10/12; A23K 10/18; C12N 1/12; C12N 1/125; C12R 2001/89
See application file for complete search history.

(56) References Cited

FOREIGN PATENT DOCUMENTS

| | | | |
|---|---|---|---|
| CN | 101519676 A | | 9/2009 |
| CN | 102160604 A | | 8/2011 |
| CN | 106987528 A | * | 7/2017 |
| CN | 106987528 A | | 7/2017 |
| CN | 107455331 A | | 12/2017 |
| JP | 2014-524745 A | | 9/2014 |

OTHER PUBLICATIONS

Chin et al., Australian Journal of Agricultural Research, 2006, 57:13-20. (Year: 2006).*
First Office Action issued in corresponding Japanese Application No. 2020-529495; dated Dec. 21, 2021; 10 pgs.
International Search Report issued in corresponding International Application No. PCT/CN2018/115327, dated Feb. 12, 2019, pp. 1-2, The State Intellectual Intellectual Property Office of the P.R. China, Beijing, China.
Chinese Office Action issued in corresponding Chinese Application No. 201810297773.9, dated Mar. 30, 2020, pp. 1-8, The State Intellectual Intellectual Property Office of the P.R. China, Beijing, China.
Second Office Action issued in corresponding Chinese Application No. 201810297773.9, dated Sep. 17, 2020, The State Intellectual Intellectual Property Office of the P.R. China, Beijing, China; 12 pgs.

* cited by examiner

*Primary Examiner* — Allison M Fox
*Assistant Examiner* — Qing Xu
(74) *Attorney, Agent, or Firm* — Hauptman Ham, LLP

(57) ABSTRACT

The invention discloses the use of the *Schizochytrium limacinum* and its preparation in improving the quality and yield of animal product. The deposit number of *Schizochytrium limacinum* in the present invention is CGMCC No. 13746 in the China General Microbiological Culture Collection Center. The *Schizochytrium limacinum* powder produced by the *Schizochytrium limacinum* may increase the DHA content in an animal product, reduce the cholesterol content in an animal product, and also improve the egg production performance of poultry. This animal product with high DHA content from natural sources is organic, safe, stable, and easy to be absorbed. It may be used as a safer and effective way for people to ingest natural DHA, and it may also cater to and meet consumer needs. Thus, *Schizochytrium limacinum* and *Schizochytrium limacinum* powder of the present application have a wide range of application in the field of general food and livestock breeding.

9 Claims, No Drawings
Specification includes a Sequence Listing.

SEQUENCE LISTING

```
<160> NUMBER OF SEQ ID NOS: 2

<210> SEQ ID NO 1
<211> LENGTH: 207
<212> TYPE: DNA
<213> ORGANISM: Schizochytrium limacinum

<400> SEQUENCE: 1
agccatgcat gtgtaagtat aagcgattgt actgtgagac tgcgaacggc tcattatatc    60
agtaataatt tcttcggtag tttcttttat atggatacct gcagtaattc tggaaataat   120
acatgctgta agagccctgt atggggctgc acttattaga ttgaagccga ttttattggt   180
gaatcatgat aattgagcag attgact                                       207

<210> SEQ ID NO 2
<211> LENGTH: 239
<212> TYPE: DNA
<213> ORGANISM: Schizochytrium limacinum
```

```
<400> SEQUENCE: 2
gagttctgcc tctgtccaaa aattaatcca aacagaaaca tcccatggtt tcatcggacc      60
gttcaatcgg taggtgcgac gggcggtgtg tacaaagggc agggacgtat tcaatgcaag     120
ctgatgactt gcgtttacta ggaattcctc gttggagatt aataattgca aaaatctagc     180
cccagcacga tgagcgttcc aaggattagc caggccttcc gaccaagcac tcaattcca     239
```

USE OF *SCHIZOCHYTRIUM LIMACINUM* AND ITS PREPARATION IN IMPROVING THE QUALITY AND YIELD OF ANIMAL PRODUCT

RELATED APPLICATIONS

The present application is a National Phase of International Application Number PCT/CN2018/115327, filed Nov. 14, 2018, and claims the priority of Chinese Application No. 201810300872.8, filed Apr. 4, 2018, Chinese Application No. 201810300876.6, filed Apr. 4, 2018, and Chinese Application No. 201810297773.9, filed Apr. 4, 2018.

INCORPORATION BY REFERENCE

The sequence listing provided in the file entitled Sequence_Listing_2021-01-15, which is an ASCII text file that was created on Feb. 3, 2021, and which comprises 994 bytes, is hereby incorporated by reference in its entirety.

TECHNICAL FIELD

The invention relates to use of *Schizochytrium limacinum* and its preparation in improving the quality and yield of animal product in agricultural organisms.

BACKGROUND OF THE INVENTION

DHA (docosahexaenoic acid) belongs to the ω-3 series of polyunsaturated fatty acids (ω-3 PUFAs). It is an important component of cell membranes and nerve tissues in human. It has the physiology functions of strengthening brain and intelligence, promoting the development of optic nerve, and preventing and treating senile dementia. It also plays an important role in promoting the growth and development of infants and young children, preventing cardiovascular diseases, inhibiting and treating certain cancers, and ensuring the normal functioning of the nervous system.

With the improvement of standards of living and consumption and the continuous deepening of research on DHA physiological functions, more and more attention has been paid to the problem of DHA intake of different populations. According to the "Chinese DHA Consumption Survey" completed by the China Food Association, the daily intake of direct DHA from food by the Chinese public is only about 40 mg, which is in a state of severe "starvation" of DHA. Obtaining DHA from the diet has become a consensus. Among them, dairy products are particularly common. The demand for milk products such as milk and goat milk rich in high-quality DHA is increasing every year. Ingesting high-quality DHA from dairy products has become a trend.

The DHA content in ordinary milk is extremely low, which is difficult to meet daily needs for people. However, the external addition of DHA in dairy products requires many materials and consumes the production cost of the enterprise. The process of adding DHA tends to cause DHA depreciate, decomposition or odor generation. By appropriately increasing the intake of polyunsaturated fatty acids such as DHA in ruminant diets, the DHA content in milk and muscle tissue may be increased, but the special digestive structure of ruminants makes most of polyunsaturated fatty acids such as DHA are converted into saturated fatty acids in rumen, which greatly reduces the utilization of DHA and other polyunsaturated fatty acids. The protection technology of fatty acids in rumen on the market mainly includes coating, hydrogenation, calcification, and the like. However, the process technology is difficult, the production cost is very high, and a syndrome of a reduction in dietary intake, a decrease in digestion and absorption rate, and a decline in milk fat is caused. Further, defects such as toxic side effects may be caused. Therefore, how to increase the DHA content in the milk of mammals, especially ruminants, and the further use of ruminant organisms to transform and produce natural organic milk rich in DHA is a problem that needs to be solved urgently.

Phosphatidylserine (PS) is a natural phospholipid. The structure of PS determines its unique amphiphilic properties. The negatively charged end is hydrophilic (or water-soluble), and the other end composed of fatty acids is lipophilic (or fat-soluble). Studies have shown that PS may be used as a carrier for DHA. When DHA is bound to the position 2 of phosphatidylserine glycerol skeleton, the stability of DHA is higher and it is easier to pass the blood-brain barrier. When DHA and PS are absorbed in the form of 2-DHA-PS (i.e., Sn-2 DHA) in vitro, they are finally converted into DHA-PS in the brain for neuroprotection. 2-DHA-PS may have biological function of both DHA and PS. Therefore, how to increase the DHA content in eggs to enrich the sources of different types of DHA and expand the use field and consumption scope of DHA is a problem that needs to be solved.

SUMMARY OF THE INVENTION

The technical problem to be solved by the present invention is how to improve the quality and yield of an animal product.

In order to solve the above technical problem, the present invention first provides any of the following uses of *Schizochytrium limacinum* or its preparations:

A1) use in improving the quality of an animal product;
A2) use in producing substances that improve the quality of an animal product;
A3) use in increasing the yield of an animal product;
A4) use in producing substances that increase the yield of an animal product.

In the above uses, the *Schizochytrium limacinum* may be *Schizochytrium limacinum* HS01, and the *Schizochytrium limacinum* HS01 has a deposit number of CGMCC No. 13746 in the China General Microbiological Culture Collection Center.

The active ingredient of the preparation may be the *Schizochytrium limacinum*.

In the above uses, the improvement of the quality of the animal product may be an increase of the DHA content in the animal product and/or an increase of the Sn-2 DHA content in the animal product and/or a reduction of the cholesterol content in the animal product.

In the above uses, the preparation may be *Schizochytrium limacinum* powder.

In the above uses, the preparation may be produced according to a method including the following steps (this method is referred to as the production method of *Schizochytrium limacinum* preparation): culturing the *Schizochytrium limacinum* to obtain a fermentation broth; using the fermentation broth to obtain the preparation.

In the above uses, the culture of the *Schizochytrium limacinum* may be carried out using a fermentation medium composed of a solvent and a solute. The solvent is water. The solute and their concentrations are 60-150 g/L of glucose, 8-25 g/L of yeast extract, 3-8 g/L of yeast powder, 5-20 g/L of $Na_2SO_4$, 0.5-1.5 g/L of KCl, 1.0-3.0 g/L of $MgSO_4$, 0.5-2.5 g/L of $K_2SO_4$, 1.0-2.0 g/L of $KH_2PO_4$, 2.0-5.0 g/L of $(NH_4)_2SO_4$, 0.5-2.5 g/L of $CaCl_2$), 0.001-0.02 g/L of $CuSO_4$, 0.001-0.02 g/L of $ZnSO_4$, 0.001-0.06 g/L of biotin, 0.1-10 g/L of starch and 0-20 g/L of protein powder, respectively, and the pH is 4.5-6.5.

The starch may be corn starch or sodium starch octenyl succinate, and the protein powder may be pea protein powder or whey protein powder. The pH of the fermentation medium may specifically be 6.

The pea protein powder is the total pea protein extracted from pea.

The whey protein powder is the total milk protein extracted from milk.

The solute and its concentration of the fermentation medium may specifically be as follows n1) or n2) or n3) or n4):

n1) 60 g/L of glucose, 8 g/L of yeast extract, 3 g/L of yeast powder, 5 g/L of $Na_2SO_4$, 0.5 g/L of KCl, 1.0 g/L of $MgSO_4$, 0.5 g/L of $K_2SO_4$, 1.0 g/L of $KH_2PO_4$, 2.0 g/L of $(NH_4)_2SO_4$, 0.5 g/L of $CaCl_2$), 0.001 g/L of $CuSO_4$, 0.001 g/L of $ZnSO_4$, 0.001 g/L of biotin and 0.1 g/L of corn starch;

n2) 150 g/L of glucose, 25 g/L of yeast extract, 8 g/L of yeast powder, 20 g/L of $Na_2SO_4$, 1.5 g/L of KCl, 3.0 g/L of $MgSO_4$, 2.5 g/L of $K_2SO_4$, 2.0 g/L of $KH_2PO_4$, 5.0 g/L of $(NH_4)_2SO_4$, 2.5 g/L of $CaCl_2$), 0.02 g/L of $CuSO_4$, 0.02 g/L of $ZnSO_4$, 0.06 g/L of biotin, 10 g/L of corn starch and 20 g/L of pea protein powder, n3) 60 g/L of glucose, 8 g/L of yeast extract, 3 g/L of yeast powder, 5 g/L of $Na_2SO_4$, 0.5 g/L of KCl, 1.0 g/L of $MgSO_4$, 0.5 g/L of $K_2SO_4$, 1.0 g/L of $KH_2PO_4$, 2.0 g/L of $(NH_4)_2SO_4$, 0.5 g/L of $CaCl_2$), 0.001 g/L of $CuSO_4$, 0.001 g/L of $ZnSO_4$, 0.001 g/L of biotin and 0.1 g/L of sodium starch octenyl succinate;

n4) 150 g/L of glucose, 25 g/L of yeast extract, 8 g/L of yeast powder, 20 g/L of $Na_2SO_4$, 1.5 g/L of KCl, 3.0 g/L of $MgSO_4$, 2.5 g/L of $K_2SO_4$, 2.0 g/L of $KH_2PO_4$, 5.0 g/L of $(NH_4)_2SO_4$, 2.5 g/L of $CaCl_2$), 0.02 g/L of $CuSO_4$, 0.02 g/L of $ZnSO_4$, 0.06 g/L of biotin, 10 g/L of sodium starch octenyl succinate and 20 g/L of whey protein powder.

In the above uses, the production of the preparation using the fermentation broth may include drying the fermentation broth to obtain the preparation.

The above method may further include adding an antioxidant to the fermentation broth after obtaining the fermentation broth, and then drying to obtain the *Schizochytrium limacinum* powder (i.e., the preparation).

The antioxidant may be an oil-soluble antioxidant and/or a water-soluble antioxidant.

The oil-soluble antioxidant may be rosemary, natural mixed tocopherol, polyphenols, and/or ascorbyl palmitate. The water-soluble antioxidant may be phytic acid, ascorbic acid and/or erythorbic acid.

When the antioxidant is composed of several different specific antioxidants, there is no requirement for the ratio between the components, and it may be adjusted according to specific needs.

The antioxidant may specifically be a mixed antioxidant composed of natural mixed tocopherol, rosemary, polyphenols, erythorbic acid and phytic acid. The mixing ratio of each substance in the mixed antioxidant may be the following p1), p2), p3) or p4):

p1) the mass ratio of natural mixed tocopherol, rosemary, polyphenols, erythorbic acid and phytic acid is 20:2:10:10:2;

p2) the mass ratio of natural mixed tocopherol, rosemary, polyphenols, erythorbic acid and phytic acid is 40:3:20:20:4;

p3) the mass ratio of natural mixed tocopherol, rosemary, polyphenols, erythorbic acid and phytic acid is 60:2:40:30:6;

p4) the mass ratio of natural mixed tocopherol, rosemary, polyphenols, erythorbic acid and phytic acid is 80:2:40:40:8.

The drying may be spray drying or drum drying or freeze drying.

The above method may further include washing the *Schizochytrium limacinum* in the fermentation broth. The above method may further include adding the antioxidant to the washed *Schizochytrium limacinum* and then drying.

The amount of dissolved oxygen in the culture may be 0 to 80% (such as 10-80%). The temperature of the culture may be 20-30° C. The culture time may be 72-120 h.

In the above uses, the animal may be a1) or a2) or a3):
 a1) poultry;
 a2) chicken;
 a3) Beijing white chicken, Hy-Line white chicken, Hy-Line Variety of brown chicken or Hy-Line variety of pink chicken.

The animal product may be eggs produced by the animal.

In the above uses, the animal may be b1) or b2):
 b1) ruminants;
 b1) cows.

The cow may be a dairy cow. The dairy cow may be a Holstein dairy cow.

The animal product may be the milk of the animal, such as milk.

A production method of the *Schizochytrium limacinum* preparation also falls within the protection scope of the present invention.

Any one of the following products also falls within the protection scope of the present invention:
 Y1) the medium for cultivating the *Schizochytrium limacinum* is the fermentation medium;
 Y2) the preparation.

In order to solve the above technical problem, the present invention also provides a method for improving the quality of animal product. The method includes feeding animal with *Schizochytrium limacinum* or its preparation to improve the quality of the animal product.

The *Schizochytrium limacinum* may be the *Schizochytrium limacinum* HS01.

The active ingredient of the preparation may be the *Schizochytrium limacinum*.

In the above method, the improvement of the quality of the animal product may be c1) and/or c2) and/or c3):
 c1) increase the DHA content in the animal product;
 c2) increase the Sn-2 DHA content in the animal product;
 c3) reduce the cholesterol content in the animal product.

In the above method, the animal may be a ruminant, and a feeding amount of the *Schizochytrium limacinum* or its preparation may be any one of d1)-d7):
 d1) 50-500 mg/day/head;
 d2) 50-250 mg/day/head;
 d3) 75-250 mg/day/head;
 d4) 100-250 mg/day/head;
 d5) 125-250 mg/day/head;
 d6) 150-250 mg/day/head;
 d7) 200-250 mg/day/head.

The animal may be poultry, and the mass content of *Schizochytrium limacinum* or its preparation in the food fed to the animal may be any one of e1)-e3):
 e1) 0.5%-2.5%;
 e2) 0.5%-1.5%;
 e3) 1%-1.5%.

The animal is poultry, and the food of the animal is composed of a basic diet and the *Schizochytrium limacinum* or its preparation. The basic diet may be a corn-soybean diet.

In the above method, the ruminant may be cow.

The cow may be a dairy cow. The cow may be a Holstein dairy cow.

The animal product may be the milk of the animal, such as milk.

In the above method, the poultry may be a2) or a3):
a2) chicken;
a3) Beijing white chicken, Hy-Line white chicken, Hy-Line Variety of brown chicken or Hy-Line variety of pink chicken.

The animal product may be eggs produced by the animal.

In the above method, the preparation may be produced using the production method of the *Schizochytrium limacinum* preparation.

Animal products produced by using the method for improving the quality of animal products or products obtained by processing the animal product also fall within the protection scope of the present invention.

In the above products, the animal is b1) or b2):
b1) ruminants;
b1) cows;
The animal product is milk.

Among the above products, the product obtained by processing the animal product is any one of f1)-f6):
f1) native DHA dairy products easy to be absorbed;
f2) native DHA pure milk;
f3) native DHA pasteurized milk;
f4) native DHA yogurt;
f5) native DHA milk powder;
f6) yogurt.

In the above products, the animal is a1) or a2) or a3):
a1) poultry;
a2) chicken;
a3) Beijing white chicken, Hy-Line white chicken, Hy-Line Variety of brown chicken or Hy-Line variety of pink chicken;
The animal product is an egg.

In the above product, the product obtained by processing the animal product is a native phospholipid DHA egg product.

In order to solve the above technical problems, the present invention also provides a method for increasing the yield of an animal product. The method includes feeding the animal with *Schizochytrium limacinum* or its preparation to increase the yield of the animal product.

The *Schizochytrium limacinum* may be the *Schizochytrium limacinum* HS01.

The active ingredient of the preparation may be the *Schizochytrium limacinum*.

The animal product may be an egg produced by the animal.

In the above method, the preparation may be produced by using the production method of the *Schizochytrium limacinum* preparation.

In the above method, the animal is poultry, and the mass content of the *Schizochytrium limacinum* or its preparation in the food fed to the animal is any one of e1)-e3):
e1) 0.5%-5%;
e2) 0.5%-1.5%;
e3) %-1.5%.

In the above method, the poultry may be a2) or a3):
a2) chicken;
a3) Beijing white chicken, Hy-Line white chicken, Hy-Line Variety of brown chicken or Hy-Line variety of pink chicken.

In the present invention, the preparation may further include a carrier. The carrier may be a solid carrier or a liquid carrier. The solid carrier may be a mineral material, a plant material or a polymer compound. The mineral material may be at least one of clay, talc, kaolin, montmorillonite, white carbon, zeolite, silica and diatomaceous earth. The plant material may be at least one of corn flour, soybean flour and starch. The polymer compound may be polyvinyl alcohol and/or polyglycol. The liquid carrier may be an organic solvent, vegetable oil, mineral oil or water. The organic solvent may be decane and/or dodecane. In the fungicide, the active ingredient may be in the form of living cells to be cultured, fermentation broth of living cells, filtrate of cell culture, or a mixture of cells and filtrate. The dosage form of the composition may be a variety of dosage forms, such as liquid, emulsion, suspension, powder, granule, wettable powder or water dispersible granule. Specifically, the *Schizochytrium limacinum* preparation may be *Schizochytrium limacinum* powder.

Biological Material Deposition Statement

Classification and naming of biological material: *Schizochytrium limacinum*

Strain number of biological material: HS01

Name of depositary institution of biological material: China General Microbiological Culture Collection Center Short name of the depositary institution of biological material: CGMCC Address of depositary institution of biological materials: Institute of Microbiology Chinese Academy of Sciences, Building 3, No. 1 West Beichen Road, Chaoyang District, Beijing, China, Post Code: 100101;

Date of deposit of the biological material: Mar. 10, 2017

Registration number of the deposit center of the biological material: CGMCC No. 13746.

BEST MODE OF IMPLEMENTING THE INVENTION

The present invention will be further described in detail below referring to specific embodiments, and the examples provided are only to illustrate the present invention, not to limit the scope of the present invention. Unless otherwise specified, the experimental methods in the following examples are conventional methods. Unless otherwise specified, the materials, reagents, and instruments used in the following examples are commercially available. In the following quantitative experiments, three repeated experiments are carried out, and the results are averaged.

Screening liquid medium: dissolve 50 g of glucose and 15 g of yeast powder in 1 L of mixed solution (obtained by mixing 1 part by volume of natural seawater and 1 part by volume of distilled water), and the pH is natural.

Screening plate: pour the screening solid medium at about 55° C. into a petri dish, and cool to obtain a solid plate.

Fermentation medium: 60 g of glucose, 10 g of glutamic acid or sodium glutamate, 10 g of corn syrup dry powder, 14 g of $NaSO_4$, 0.5 g of KCl, 2.0 g of $MgSO_4$, 1.0 g of $K_2SO_4$, 1.0 g of $KH_2PO_4$, 1.0 g of $(NH_4)_2SO_4$ and 0.5 g of $CaCl_2$) is dissolved in 1 L of distilled water, and the pH is adjusted to 6.0.

Malt juice agar medium: dissolve 150 g of malt infusion powder in 1 L of mixed solution (composed of 1 part by volume of natural seawater and 1 part of volume of distilled water), and the pH value is natural; then add agar powder to a concentration of 15 g/100 mL, to obtain a medium.

Natural mixed tocopherol is a product of ADM company, with the product number of MTS-90. Rosemary is a product of Guangzhou Branch of Kenaiou Trading (Shanghai) Co., Ltd., with the product number of ROSEMARY 41-19-58. Polyphenol is a product of Fujian Likangyuan Biological Engineering Co., Ltd., with the product number of TP-98. Erythorbic acid is a product of Zhengzhou Tuoyang Experimental Co., Ltd., with the content is ≥98%. Phytic acid is a product of Laiyang Wanjiwei Biological Engineering Co., Ltd.

Example 1. Separation and Identification of *Schizochytrium limacinum* HS01

I. Separation of HS01

1. *Schizochytrium limacinums* from a number of mangroves in Yunxiao County, Zhangzhou City, Fujian Province is collected by the inventor of the present application, and mixed to obtain a mixed solution. 0.5 mL of the mixed solution are inoculated into 5 mL of the screening liquid medium, and then cultured at 25° C., 200 rpm/min for 2 days, to obtain a cultured bacterial solution.

2. The cultured bacterial solution obtained in step 1 is spread evenly on the screening plate and incubated at 25° C. for 2 days to produce a single colony.

3. After step 2 is completed, single colonies are picked and inoculated into 5 mL of fermentation medium, and then cultured at 25° C., 200 rpm/min for 2 days to obtain a cultured bacterial solution.

4. Take the cultured bacterial solution obtained in step 3, centrifuge at 4° C., 2000 rpm for 5 min, and collect bacteria.

5. Take 1.0-2.0 g of bacteria into a measuring cylinder with stopper (the specification is 100 mL), add 15 mL of HCl aqueous solution (with the concentration of 8.3 mol/L) first, close the lid, and place it in a water bath at 70-80° C. and hydrolyze for 50-60 minutes (during this period, measuring cylinder is placed on a vortex mixer and shaken once every 10 minutes); after cooling to room temperature, first add 10 mL of 95% (v/v) ethanol aqueous solution, shake fully and then add 20 mL of anhydrous ether to fully shake and extract for 1-2 minutes, and finally add 20 mL of petroleum ether, shake fully and extract for 1-2 minutes, let stand for layering, place the upper organic phase in a glass weighing dish, which has been dried and the empty weight thereof has been weighed, and place the glass weighing dish on a boiling water bath in a fume hood to fully evaporate the organic phase (be sure to fully evaporate), and the liquid phase is the grease.

6. Take the grease extracted in step 5 and detect the DHA content according to GB 26400-2011 National Food Safety Standard, and the composition and content of fatty acid according to the method of AOAC996.06.

Strains with higher DHA content are selected and purified repeatedly 24 times. A strain of *Schizochytrium limacinum* strain screened is named *Schizochytrium limacinum* HS01.

The *Schizochytrium limacinum* HS01 is inoculated into the fermentation medium for monoclonal culturing 12 consecutive passages and the DHA content is detected according to the above steps. The results show that the stability of the *Schizochytrium limacinum* HS01 for producing DHA is good.

II. Identification of the *Schizochytrium limacinum* HS01

1. Morphological Identification

The *Schizochytrium limacinum* HS01 is inoculated on the wort agar medium and cultured in the dark at 25° C. After 5 days, the morphology of the colonies is observed and the morphological characteristics of the cells are observed by high-resolution transmission electron microscopy.

The results show that the colony diameter of the *Schizochytrium limacinum* HS01 is 2-4.3 mm, white (light orange in the later period), and the edges are uneven; the bacteria proliferated in a fission manner, the cell wall is thin, spherical, colorless or light orange, transparent, with a size of 4.5-15.5 μm. Zoospores and exoplasmic reticulum are not seen.

2. 18s rDNA sequence homology analysis

The partial sequence of the 18s rDNA of the *Schizochytrium limacinum* HS01 is shown as SEQ ID No. 1 in the sequence listing.

The partial sequence of the 18s rDNA of the *Schizochytrium limacinum* HS01 is shown as SEQ ID No. 2 in the sequence listing.

Combining the above identification results, the *Schizochytrium limacinum* HS01 is a *Schizochytrium limacinum*.

III. Deposition of *Schizochytrium limacinum* HS01

*Schizochytrium limacinum* HS01 is deposited on Mar. 10, 2017 at China General Microbiological Culture Collection Center (CGMCC for short, address: Building 3, No. 1 West Beichen Road, Chaoyang District, Beijing, China). The deposition number is CGMCC No. 13746.

Example 2. Production of *Schizochytrium limacinum* Powder

The procedure for producing *Schizochytrium limacinum* powder by using *Schizochytrium limacinum* HS01 in Example 1 is as follows. The experiment is repeated three times, and the results are averaged:

I. Production of a Culture Medium

Shake flask medium 1 is composed of a solute and a solvent. The solvent is water. The solute and their concentrations are 60 g/L of glucose, 5 g/L of yeast extract, respectively. Shake flask medium 2 is composed of a solute and a solvent. The solvent is water. The solute and their concentrations are 150 g/L of glucose and 25 g/L of yeast extract, respectively.

Seed medium 1 is composed of a solute and a solvent. The solvent is water. The solute and their concentrations are 60 g/L of glucose, 8 g/L of yeast extract, 3 g/L of yeast powder, 5 g/L of $Na_2SO_4$, 0.5 g/L of KCl, 1.0 g/L of $MgSO_4$, 0.5 g/L of $K_2SO_4$, 1.0 g/L of $KH_2PO_4$, 2.0 g/L of $(NH_4)_2SO_4$, 0.5 g/L of $CaCl_2$), 0.001 g/L of $CuSO_4$, 0.001 g/L of $ZnSO_4$. After the production is completed, the initial pH is adjusted to 6.0 with alkali (sodium hydroxide solution or ammonia water). The seed medium 2 is composed of a solute and a solvent. The solvent is water. The solute and their concentrations are 150 g/L of glucose, 25 g/L of yeast extract, 8 g/L of yeast powder, 20 g/L of $Na_2SO_4$, 1.5 g/L of KCl, 3.0 g/L of $MgSO_4$, 2.5 g/L of $K_2SO_4$, 2.0 g/L of $KH_2PO_4$, 5.0 g/L of $(NH_4)_2SO_4$, 2.5 g/L of $CaCl_2$), 0.02 g/L of $CuSO_4$, 0.02 g/L of $ZnSO_4$, After the production is completed, the initial pH is adjusted to 6.0 with alkali (sodium hydroxide solution or ammonia water).

Fermentation medium 1 is composed of a solute and a solvent. The solvent is water. The solute and their concentrations are 60 g/L of glucose, 8 g/L of yeast extract, 3 g/L of yeast powder, 5 g/L of $Na_2SO_4$, 0.5 g/L of KCl, 1.0 g/L of $MgSO_4$, 0.5 g/L of $K_2SO_4$, 1.0 g/L of $KH_2PO_4$, 2.0 g/L of $(NH_4)_2SO_4$, 0.5 g/L of $CaCl_2$), 0.001 g/L of $CuSO_4$, 0.001 g/L of $ZnSO_4$, 0.001 g/L of biotin, 0.1 g/L of corn starch. After the production is completed, the initial pH is adjusted to 6.0 with alkali (sodium hydroxide solution or ammonia water). Fermentation medium 2 is composed of a solute and a solvent. The solvent is water. The solute and their concentrations are 150 g/L of glucose, 25 g/L of yeast extract, 8 g/L of yeast powder, 20 g/L of $Na_2SO_4$, 1.5 g/L of KCl, 3.0 g/L of $MgSO_4$, 2.5 g/L of $K_2SO_4$, 2.0 g/L of $KH_2PO_4$, 5.0 g/L of $(NH_4)_2SO_4$, 2.5 g/L of $CaCl_2$), 0.02 g/L of $CuSO_4$, 0.02 g/L of $ZnSO_4$, 0.06 g/L of biotin, 10 g/L of corn starch, 20 g/L of pea protein powder. After the production is completed, the initial pH is adjusted to 6.0 with alkali (sodium hydroxide solution or ammonia water). Fermentation medium 3 is composed of a solute and a solvent. The solvent is water. The solute and their concentrations are 60 g/L of glucose, 8 g/L of yeast extract, 3 g/L of yeast powder, 5 g/L of $Na_2SO_4$, 0.5 g/L of KCl, 1.0 g/L of $MgSO_4$, 0.5 g/L of $K_2SO_4$, 1.0 g/L of $KH_2PO_4$, 2.0 g/L of $(NH_4)_2SO_4$, 0.5 g/L of $CaCl_2$), 0.001 g/L of $CuSO_4$, 0.001 g/L of $ZnSO_4$, 0.001 g/L of biotin, 0.1 g/L of sodium starch octenyl succinate. After the production is completed, the initial pH is adjusted to 6.0 with alkali (sodium hydroxide solution or ammonia water). Fermentation medium 4 is composed of a solute and a solvent. The solvent is water. The solute and their concentrations are 150 g/L of glucose, 25 g/L of yeast extract, 8 g/L of yeast powder, 20 g/L of $Na_2SO_4$, 1.5 g/L of KCl, 3.0 g/L of $MgSO_4$, 2.5 g/L of $K_2SO_4$, 2.0 g/L of $KH_2PO_4$, 5.0 g/L of $(NH_4)_2SO_4$, 2.5 g/L of $CaCl_2$), 0.02 g/L of $CuSO_4$, 0.02 g/L of $ZnSO_4$, 0.06 g/L of biotin, 10 g/L of sodium starch octenyl succinate, 20 g/L of whey protein powder. After the production is completed, the initial pH is adjusted to 6.0 with alkali (sodium hydroxide solution or ammonia water).

II. Production and Indicator Detection of *Schizochytrium limacinum* Powder

1. Production

Inoculate *Schizochytrium limacinum* HS01 into the shake flask medium 1 and incubate at 200 rpm and a temperature of 20° C. for 24 h to obtain a shake flask culture solution 1; inoculate the shake flask culture solution 1 into the seed medium 1, and culture for 48 h under a condition of 10-80% of dissolved oxygen (dissolved oxygen is a dynamic process during the growth process) and a temperature of 20° C. During the culture, the pH of the culture solution is maintained between 4.5 and 6.5. The pH will decrease during the fermentation, and it may be adjusted by ammonia or sodium hydroxide solution to obtain a seed culture solution 1. Inoculate the seed culture solution 1 into the fermentation medium 1 at an inoculation amount of 10%, and culture under a condition of 10-80% dissolved oxygen (dissolved oxygen is a dynamic process during the growth process) and a temperature of 20° C. for 120 h to obtain a fermentation broth, recorded as fermentation broth 1. During the culture, the pH of the culture solution is maintained between 4.5 and 6.5. The pH will decrease during the fermentation, and it may be adjusted by ammonia or sodium hydroxide solution.

Inoculate *Schizochytrium limacinum* HS01 into the shake flask medium 2 and culture at 400 rpm and 30° C. for 48 h to obtain a shake flask culture solution 2; inoculate the shake flask culture solution 2 into the seed medium 2, culture for 24 h under a condition of 10-80% of dissolved oxygen and a temperature of 30° C. During the culture, the pH of the culture solution is maintained between 4.5 and 6.5. The pH will decrease during the fermentation, and it may be adjusted by ammonia or sodium hydroxide solution, to obtain a seed culture solution 2; inoculate the seed culture solution 2 into the fermentation medium 2 at an inoculation amount of 20%, and culture for 72 h under a condition of 10-80% of dissolved oxygen and a temperature of 30° C. to obtain a fermentation broth, referred to as a fermentation broth 2. During the culture, the pH of the culture solution is maintained between 4.5 and 6.5. The pH will decrease during the fermentation, and it may be adjusted by ammonia or sodium hydroxide solution.

Inoculate the *Schizochytrium limacinum* HS01 into the shake flask medium 1 and culture at 200 rpm and a temperature of 20° C. for 24 h to obtain a shake flask culture solution 1. Inoculate the shake flask culture solution 1 into a seed medium 1, and culture for 48 h under a condition of 10-80% of dissolved oxygen and a temperature of 20° C. During the culture, the pH of the culture solution is maintained between 4.5 and 6.5. The pH will decrease during the fermentation, and it may be adjusted by ammonia or sodium hydroxide solution to obtain a seed culture solution 1. Inoculate the seed culture solution 1 into the fermentation medium 3 at an inoculation amount of 10%, and culture for 120 h under a condition of 0 to 80% of dissolved oxygen and a temperature of 20° C. to obtain a fermentation broth, referred to as a fermentation broth 3. During the culture, the pH of the culture solution is maintained between 4.5 and 6.5. The pH will decrease during the fermentation, and it may be adjusted by ammonia or sodium hydroxide solution.

Inoculate the *Schizochytrium limacinum* HS01 into a shake flask medium 2 and culture at 400 rpm and 30° C. for 24 h to obtain a shake flask culture solution 2. Inoculate the shake flask culture solution 2 into a seed medium 2, and culture for 24 h under a condition of 10-80% of dissolved oxygen and a temperature of 30° C. During the culture, the pH of the culture solution is maintained between 4.5 and 6.5. The pH will decrease during the fermentation, and it may be adjusted by ammonia or sodium hydroxide solution to obtain a seed culture solution 2. Inoculate the seed culture solution 2 into a fermentation medium 4 at an inoculation amount of 20%, and culture for 72 h under a condition of 10-80% of dissolved oxygen and a temperature of 30° C. to obtain a fermentation broth, referred to as a fermentation broth 4. During the culture, the pH of the culture solution is maintained between 4.5 and 6.5. The pH of the fermentation process will decrease, and the pH is adjusted by ammonia or sodium hydroxide solution.

After the fermentation is completed, an antioxidant 1 (the antioxidant 1 is composed of natural mixed tocopherol, rosemary, polyphenols, erythorbic acid and phytic acid, wherein the mass ratio of natural mixed tocopherol, rosemary, polyphenols, erythorbic acid and phytic acid is 20:2:10:10:2) is added to the fermentation broth 1 to obtain a mixed solution, in which the content of natural mixed tocopherol, rosemary, polyphenols, erythorbic acid and phytic acid by mass percentage are 0.2%, 0.02%, 0.1%, 0.1% and 0.02%, respectively. The mixed solution is emulsified and mixed to obtain a stable fermentation broth 1. The stable fermentation broth 1 is pasteurized and then sprayed, roller or freeze-dried to obtain a *Schizochytrium limacinum* powder 1.

Add an antioxidant 2 (the antioxidant 2 is composed of mixed natural tocopherols, rosemary, polyphenols, erythorbic acid and phytic acid, wherein the mass ratio of mixed natural tocopherols, rosemary, polyphenols, erythorbic acid and phytic acid is 40:3:20:20:4) to the fermentation broth 2, to obtain a mixed solution, in which the content of natural mixed tocopherol, rosemary, polyphenol, erythorbic acid and phytic acid by mass percentage are 0.4%, 0.03%, 0.2%, 0.2% and 0.04%, respectively. The mixed solution is emulsified and mixed to obtain a stable fermentation broth 2. The stable fermentation broth 2 is pasteurized and then sprayed, roller or freeze-dried to obtain a *Schizochytrium limacinum* powder 2.

Centrifuge the fermentation broth 3 to collect *Schizochytrium limacinum* cell slurry, add the same volume of sterile deionized water according to the volume of *Schizochytrium limacinum* cell slurry, and then centrifuge, repeat washing 2 to 3 times to obtain a *Schizochytrium limacinum* cell slurry. Add an antioxidant 3 (the antioxidant 3 is composed of natural mixed tocopherol, rosemary, polyphenols, erythorbic acid and phytic acid, wherein the mass ratio of natural mixed tocopherol, rosemary, polyphenols, erythorbic acid and phytic acid is 60:2:40:30:6) into the *Schizochytrium limacinum* cell slurry to obtain a mixture, in which the content of natural mixed tocopherol, rosemary, polyphenols, erythorbic acid and phytic acid by mass percentage is 0.6%, 0.02%, 0.4%, 0.3% and 0.06%, respectively. The mixture is emulsified and mixed to obtain a stable cell slurry. The stable cell slurry is pasteurized and then dried (one of the following three is selected: spray, roller or freeze-drying), to obtain a *Schizochytrium limacinum* powder, referred to as a *Schizochytrium limacinum* powder 3.

The fermentation broth 4 is centrifuged to collect a *Schizochytrium limacinum* cell slurry, add the same volume of sterile deionized water according to the volume of *Schizochytrium limacinum* cell slurry, and then centrifuge, repeat washing 2 to 3 times to obtain the *Schizochytrium limacinum* cell slurry. Add an antioxidant 4 (the antioxidant 4 is composed of mixed natural tocopherols, rosemary, polyphenols, erythorbic acid and phytic acid, in which the mass ratio of mixed natural tocopherols, rosemary, polyphenols, erythorbic acid and phytic acid is 80:2:40:40:8) into the *Schizochytrium limacinum* cell slurry to obtain a mixture. The content of natural mixed tocopherol, rosemary, polyphenols, erythorbic acid and phytic acid in the mixture by mass percentage is 0.8%, 0.02%, 0.4%, 0.4% and 0.08%, respectively. The mixture is emulsified and mixed to obtain a stable cell slurry. The stable cell slurry is pasteurized and then dried (one of the following three is selected: spray, roller or freeze-drying) to obtain a *Schizochytrium limacinum* powder, referred to as *Schizochytrium limacinum* powder 4.

2. Indicator Detection

The content of protein, moisture, fatty acid, ash and DHA of *Schizochytrium limacinum* powders 1-4 obtained in step 1 is detected respectively. The specific detection methods are as follows:

Protein detection is carried out according to GB 5009.9 "National Food Safety Standards Determination of Protein in Food".

Moisture detection is carried out according to GB 5009.3 "National Food Safety Standards Determination of Moisture in Food".

Ash detection is carried out according to GB 5009.4 "National Food Safety Standards Determination of Ash in Food".

Fatty acid detection is carried out according to GB 5009.168 "National Food Safety Standards Determination of Fatty Acids in Foods".

DHA detection is carried out according to GB 26400 "National Food Safety Standards Food Additives Docosahexaenoic Acid Grease (Fermentation Method)".

Detection of the proportion of Sn-2 DHA to total DHA in milk and the fatty acid composition are carried out according to GB 5009.168-2016 "National Food Safety Standards Determination of Fatty Acids in Food" and GB/T 24894-2010/ISO 6800:1997.

The results show that the protein content of *Schizochytrium limacinum* powder obtained in the above step is 10-60%, the mass content of moisture 0.5-3.0%, the content of ash is 3-12%, and the mass content of the fatty acid is 25-50%. Among fatty acids, the mass content of unsaturated fatty acid DHA is 10-24%, the mass content of DPA is 2.0-6.0%, and the mass content of EPA is 0.1-0.5%.

TABLE 1

| | Indicator | *Schizochytrium limacinum* powder 1 | *Schizochytrium limacinum* powder 2 | *Schizochytrium limacinum* powder 3 | *Schizochytrium limacinum* powder 4 |
|---|---|---|---|---|---|
| | Protein | 20 | 25 | 30 | 45 |
| | Moisture | ≤3.0 | ≤3.0 | ≤3.0 | ≤3.0 |
| | Ash | 9.5 | 11.0 | 4.0 | 4.0 |
| Fatty acids | C8:0 Caprylic acid | 2.0 | 2.5 | 2.5 | 3.0 |
| | C10:0 Capric acid | 1.0 | 1.5 | 2.0 | 2.5 |
| | C16:0 Palmitic acid | 3.0 | 6.0 | 3.0 | 6.0 |
| | C18:0 Stearic acid | 0.5 | 0.5 | 0.5 | 0.5 |
| | C22:5 DPA | 4.5 | 4.0 | 4.0 | 3.0 |
| | C20:5 EPA | 0.2 | 0.25 | 0.25 | 0.3 |
| | C22:6 DHA | 20.0 | 17.0 | 19.5 | 20.0 |
| | Other fatty acids | 5.0 | 3.0 | 4.0 | 0.7 |

Note:
The content of each indicator in Table 1 refers to the mass percentage of each substance in the dry powder. Other fatty acids refer to C8:0 Caprylic acid, C10:0 Capric acid, C16:0 Palmitic acid, C18:0 Stearic acid, C22:5 DPA, C20:5 EPA and C22:6 Fatty acids other than DHA.

III. The Fistula Experimental Test of *Schizochytrium limacinum* Powders

Nylon bag method is used in rumen fistula experiment of *Schizochytrium limacinum* powders 1 and 2. The operation steps are as follows:

1. Test Animals and Diets

Dairy cows (Holstein dairy cows) possess a permanent gastric fistula. The pre-feeding period is 7 days. During this period, deworming is performed, and ectoparasites are expelled with 1% trichlorfon. 0.8 mg/kg body weight of levamisole hydrochloride is orally administrated to expel internal parasites. Dairy cows are bred under a condition that the nutritional level is 1.3 times to maintain the need, twice a day in equal amounts, once at 07:00 and 16:00, respectively, and water is drunk freely after feeding.

2. Production of Samples

*Schizochytrium limacinum* powders are randomly sampled by the "quartile method", dried at 65° C. to a constant weight, and put it into a milled bottle for use.

3. Production of Nylon Bag

A 300 mesh nylon cloth is cut into a 170 mm×130 mm rectangle. After folding in half, double stitch with polyester is threaded to make a nylon bag with a size of 120 mm×80 mm. Flatten the loose edges with a soldering iron. Before the test, place the nylon bag in the rumen for balancing 72 h, take it out, wash and dry it, and check it for use without any damage.

4. Test Design and Measurement Method

The rumen degradation of the nylon bag method is carried out according to the scheme proposed by the Dairy Cow Breeding Standards Research Collaboration Group, and the like. The test is designed with a random unit group, and two repeats for each cow at each time point are set.

Each nylon bag is filled with about 10 g of *Schizochytrium limacinum* powders, and the variance analysis of the samples is not significant (P>0.05). Every 2 bags are fastened to a 30 cm long semi-polyethylene tube. 2 hours later, after feeding in the morning, the nylon bag is placed in the abdominal sac of the rumen. The other end of the tube is hung on the fistula cover. 6 tubes are put into each rumen of a cow at the same time, totally 12 bags. Take a tube from the rumen of each cow at 8 time points of 0 h, 2 h, 4 h, 6 h, 12 h, 24 h, 36 h and 48 h, respectively after putting the bag, wash it with clean water and rinse it in the washing machine for 7 minutes, until the water is clear, then bake at 65° C. to a constant weight and weigh.

The determination of dry matter (DM) is carried out according to the method of GB6435-86, and the determination of DHA is undertaken by Xiamen Huisheng Biological Co., Ltd. The degradation rate of a certain nutrient at a certain time point (t) of the sample/%=(1−the mass of a certain nutrient remaining/the total mass of a nutrient put in the bag)×100%

The results are shown in Table 2. The results show that the highest degradation rate of *Schizochytrium limacinum* powder over the rumen of dairy cows is 54.7%.

TABLE 2

Fistula test results of the *Schizochytrium limacinum* powder

| | *Schizochytrium limacinum* powder 1 | | *Schizochytrium limacinum* powder 2 | |
|---|---|---|---|---|
| Time in rumen (h) | degradation rate of *Schizochytrium limacinum* powder (%) | degradation rate of DHA (%) | degradation rate of *Schizochytrium limacinum* powder (%) | degradation rate of DHA (%) |
| 0 | 18.5 | 1.0 | 14.6 | 0 |
| 2 | 37.0 | 5.2 | 33.8 | 2.0 |
| 4 | 47.5 | 5.2 | 40.7 | 3.3 |
| 6 | 50.2 | 6.0 | 44.7 | 5.0 |
| 12 | 50.6 | 7.0 | 45.7 | 6.2 |
| 24 | 53.8 | 7.0 | 47.3 | 6.5 |
| 36 | 54.7 | 10.0 | 50.9 | 8.1 |
| 48 | 54.7 | 10.0 | 50.3 | 8.5 |

Example 3. The *Schizochytrium limacinum* Powder of Example 2 May Increase the DHA Content in Milk In this example, after feeding cows with the *Schizochytrium limacinum* powder of Example 2, the DHA content in the milk is detected to determine the effect of *Schizochytrium limacinum* powders on the DHA content in the milk, and the experiment is repeated three times.

I. Feeding Methods:

60 healthy Holstein dairy cows with no significant difference in body weight and month age are selected and randomly divided into six groups with 10 heads in each group, that is, a free-range experimental group 1, a free-range experimental group 2, a free-range blank control group, a captive experimental group 1, a captive experiment group 2 and a captive blank control group.

Firstly, cows in each experimental group are bred in the pre-feeding period (the pre-feeding period is 15 days, and a large feeding amount of *Schizochytrium limacinum* powder is gradually added according to the adaptation of the cows); in the later formal feeding period, *Schizochytrium limacinum* powder is added according to a certain proportion into the feed for stirring and mixing, feeding once every 8 hours.

The *Schizochytrium limacinum* powder added to the feeds of the free-range experimental group 1 and the free-range experimental group 2 are the *Schizochytrium limacinum* powder 1 and 2 in example 1, respectively, and the *Schizochytrium limacinum* powder added to the feed of the captive experiment group 1 and the captive experiment group 2 is *Schizochytrium limacinum* powder 1 and 2 in example 1, respectively. The specific feeding method is as follows:

In the pre-feeding period, the feeding amount of the *Schizochytrium limacinum* powder in the experimental group increases gradually as follows:

The feeding amount of the *Schizochytrium limacinum* powder on days 1 and 2 of the pre-feeding period is 50 mg/day/head;

The feeding amount of the *Schizochytrium limacinum* powder on days 3 and 4 of the pre-feeding period is 75 mg/day/head;

The feeding amount of the *Schizochytrium limacinum* powder on days 5 and 6 of the pre-feeding period is 100 mg/day/head;

The feeding amount of the *Schizochytrium limacinum* powder on days 7 and 8 of the pre-feeding period is 125 mg/day/head;

The feeding amount of the *Schizochytrium limacinum* powder on days 9 and 10 of the pre-feeding period is 150 mg/day/head;

The feeding amount of the *Schizochytrium limacinum* powder on days 11 and 12 of the pre-feeding period is 200 mg/day/head;

The feeding amount of the *Schizochytrium limacinum* powder on days 13, 14 and 15 of the pre-feeding period is 250 mg/day/head.

In the formal feeding period, the feeding amount of the *Schizochytrium limacinum* powder is 250 mg/day/head.

In the blank control group, no *Schizochytrium limacinum* powder is added into the feed of cows, and the rest of the ingredients are the same as those in the experimental group. The feeding time and feeding amount are the same as that in the experimental group.

Cows in the free-range experimental group 1, the free-range experimental group 2 and the free-range blank control group are free-ranged, and there are no other edible foods for the cows in the free-range facility. The cows in the captive experimental group 1, the captive experimental group 2 and the captive blank control group are captive, without any other edible food.

II. Milk Data Detection

DHA milk sample collection: collect milk samples from all cows fed three times in the morning, noon and evening and mix and send them for inspection. According to the national standard GB5413.27-2010 Determination of fatty acids in infant food and dairy products, indicators of milk fat, milk protein, DHA content, the proportion of Sn-2 DHA in milk to the total DHA are detected.

The results (Table 3) show that no matter whether it is free-range or captive, there is no significant difference between the experimental group and the blank control group in the milk fat and milk protein content. However, after adding the *Schizochytrium limacinum* powder of Example 1, the DHA content in milk gradually increases with the increase of feeding time, and the DHA content in milk of each experimental group is significantly higher than that of the control group. There is no significant difference in DHA content between two control groups.

TABLE 3

Test results of milk DHA content (mg/100 g milk)

| Group | End of the pre-feeding period | Day 7 in the formal period | Day 15 in the formal period | Day 30 in the formal period | Day 45 in the formal period | Day 60 in the formal period | Day 75 in the formal period | After Day 75 in the formal period |
|---|---|---|---|---|---|---|---|---|
| free-range experimental group 1 | 4.0 | 5.7 | 7.9 | 8.5 | 9.0 | 12.5 | 13.0 | 20.0 |
| free-range experimental group 2 | 6.0 | 8.0 | 9.4 | 11.0 | 14.2 | 15.5 | 20.0 | 25.5 |
| free-range blank control group | 0 | 0.2 | 0.2 | 0.1 | 0.5 | 0 | 0.3 | 0.2 |
| captive experimental group 1 | 12 | 14.5 | 15.5 | 18.0 | 21.5 | 25.4 | 26.5 | 30 |
| captive experimental group 2 | 16 | 18.3 | 19.5 | 21.0 | 22.9 | 23.8 | 24.5 | 28.5 |
| captive blank control group | 0 | 0.2 | 0.2 | 0.1 | 0.5 | 0 | 0.3 | 0.2 |

Note:
The end of the pre-feeding period is the day 15 of the pre-feeding period, and the days 7, 15, 30, 45, 60 and 75 of the formal period are the day 7, 15, 30, 45, 60 and 75 of the formal feeding period, respectively. After the day 75 of the formal period means day 100.

TABLE 4

The proportion of Sn-2 DHA to total DHA in milk (%)

| Group | End of the pre-feeding period | Day 7 in the formal period | Day 15 in the formal period | Day 30 in the formal period | Day 45 in the formal period | Day 60 in the formal period | Day 75 in the formal period | After Day 75 in the formal period |
|---|---|---|---|---|---|---|---|---|
| free-range experimental group 1 | 30 | 40 | 50 | 55 | 60 | 65 | 70 | 80 |

TABLE 4-continued

The proportion of Sn-2 DHA to total DHA in milk (%)

| Group | End of the pre-feeding period | Day 7 in the formal period | Day 15 in the formal period | Day 30 in the formal period | Day 45 in the formal period | Day 60 in the formal period | Day 75 in the formal period | After Day 75 in the formal period |
|---|---|---|---|---|---|---|---|---|
| free-range experimental group 2 | 30 | 50 | 55 | 55 | 60 | 70 | 80 | 95 |
| free-range blank control group | 0 | 0 | 0 | 0 | 0 | 0 | 0 | 0 |
| captive experimental group 1 | 30 | 40 | 50 | 55 | 60 | 65 | 70 | 80 |
| captive experimental group 2 | 30 | 50 | 55 | 55 | 60 | 70 | 80 | 95 |
| captive blank control group | 0 | 0 | 0 | 0 | 0 | 0 | 0 | 0 |

Note:
There is no obvious difference between free-range groups and captive groups in the proportion of Sn-2 DHA to the total DHA in milk; and the proportion generally fluctuates in a range of 30-95% without any special rule.

Example 4. The *Schizochytrium limacinum* Powder of Example 2 May Improve Egg Quality and Laying Performance of Laying Hens In this example, after feeding the *Schizochytrium limacinum* powder of Example 2 to laying hens, the effect of *Schizochytrium limacinum* powder on the performance of laying hens and egg quality is detected.

1. Test Animals 360 healthy laying hens (Hy-Line white chicken) in laying period with no significant difference in body weight are randomly selected. There is no significant difference in the age of month among each laying hens. The laying hens are randomly divided into 4 groups (control group, 0.5% experiment group, 1.0% experimental group and 1.5% experimental group). For each group, there are 6 parallel groups, and for each parallel group, there are 15 laying hens.

2. Feeding Management 3 layers of cages and keep light are used. The experimental diet is fed in the form of dry powder, 3 times a day, free to eat and drink, and the daily intake is recorded for each cage. The basic diet for laying hens in the experimental group is a corn-soybean diet. Each experimental group is fed with the basic diet supplemented with the *Schizochytrium limacinum* powder of Example 2. The mass content of the *Schizochytrium limacinum* powder in the 0.5% experimental group is 0.5%. The mass content of the *Schizochytrium limacinum* powder in the 1.0% experimental group is 1.0%. The mass content of the *Schizochytrium limacinum* powder in the 1.5% experimental group is 1.5%. The control group is fed a basic diet. The day when the experimental group is fed with the *Schizochytrium limacinum* powder is recorded as day 1. Calculate the laying rate every day, detect the cholesterol content in eggs on day 15 and day 25 (the results on day 25 are shown in Table 5), and calculate the changes in laying rate, egg cholesterol and DHA content, the results are shown in Table 6.

TABLE 5

Determination results of laying rate, cholesterol and DHA content on day 25

| Groups | | laying rate (%) | cholesterol content (mg/100 g) | DHA content (mg/100 g) |
|---|---|---|---|---|
| control group | Parallel 1 | 88.9 | 307.43 | 33.37 |
| | parallel 2 | 90.6 | 304.54 | 32.63 |
| | parallel 3 | 94.2 | 314.35 | 35.50 |
| | parallel 4 | 93.7 | 318.72 | 37.67 |
| | parallel 5 | 86.6 | 320.31 | 39.22 |
| | parallel 6 | 95.6 | 301.43 | 37.07 |
| | mean | 91.6 | 311.1 | 35.9 |
| 0.5% Group | Parallel 1 | 85.3 | 250.07 | 142.00 |
| | parallel 2 | 84.4 | 243.58 | 163.00 |
| | parallel 3 | 89.8 | 239.43 | 145.00 |
| | parallel 4 | 91.1 | 233.75 | 147.00 |
| | parallel 5 | 93.3 | 249.37 | 146.00 |
| | parallel 6 | 81.8 | 248.61 | 157.00 |
| | mean | 87.6 | 243.1 | 150.0 |
| 1.0% Group | Parallel 1 | 96.8 | 213.85 | 259.00 |
| | parallel 2 | 98.2 | 217.24 | 244.00 |
| | parallel 3 | 92.8 | 234.06 | 241.00 |
| | parallel 4 | 96.0 | 235.23 | 263.00 |
| | parallel 5 | 94.7 | 228.09 | 242.00 |
| | parallel 6 | 95.1 | 233.84 | 245.00 |

TABLE 5-continued

Determination results of laying rate, cholesterol and DHA content on day 25

| Groups | | laying rate (%) | cholesterol content (mg/100 g) | DHA content (mg/100 g) |
|---|---|---|---|---|
| | mean | 95.6 | 227.1 | 249.0 |
| 1.5% Group | Parallel 1 | 90.2 | 250.57 | 320.00 |
| | parallel 2 | 92.8 | 243.07 | 328.00 |
| | parallel 3 | 95.1 | 227.51 | 309.00 |
| | parallel 4 | 93.7 | 250.67 | 333.00 |
| | parallel 5 | 96.4 | 224.99 | 311.00 |
| | parallel 6 | 92.8 | 230.67 | 319.00 |
| | mean | 93.5 | 237.9 | 320.0 |

TABLE 6

Changes in laying rate and egg nutrient composition on days 15 and 25

| | | Group | | | | | |
|---|---|---|---|---|---|---|---|
| | | Day 15 in experimental Group | | | Day 25 in experimental Group | | |
| Item | Day 25 in control group | 0.5% Group | 1.0% Group | 1.5% Group | 0.5% Group | 1.0% Group | 1.5% Group |
| Change in laying rate (%) | | +0.05 | +4.40 | +2.00 | +0.10 | +4.37 | +2.07 |
| Change in cholesterol (%) | | −18.54 | −22.11 | −19.46 | −21.85 | −27.02 | −23.53 |
| DHA (mg/100 g) | 35.91 | 150 | 244 | 354 | 150 | 249 | 320 |

Note:
In Table 6, "Change in laying rate" refers to the change amount compared with the laying rate of the same period of laying hens in the control group. "Change in cholesterol" refers to the change amount compared with the cholesterol content in eggs of the same period in the control group. "+" means increase, "−" means decrease.

The laying rate, egg weight, feed intake, egg-to-feed ratio on day 25 are counted, and the lipid content and cholesterol content in eggs are measured. The results are shown in Table 7.

TABLE 7

Effect of feeding different amounts of *Schizochytrium limacinum* powder on the performance of laying hens and lipid on day 25

| | Groups | | | |
|---|---|---|---|---|
| item | control group (Day 25) | 0.5% experimental Group (Day 25) | 1.0% experimental Group (Day 25) | 1.5% experimental Group (Day 25) |
| laying rate (%) | 91.6 | 87.6 | 95.6 | 93.5 |
| egg weight (g) | 56.08 | 57.11 | 56.87 | 56.61 |
| feed intake (g/hen/day) | 113.19 | 119.36 | 125.87 | 109.79 |
| egg-to-feed ratio | 2.20 | 2.38 | 2.36 | 2.15 |
| lipid content in eggs (g/100 g) | 9.16 | 10.77 | 9.28 | 11.11 |
| cholesterol content in eggs (mg/100 g) | 311.13 | 243.14 | 227.05 | 237.91 |

Significance analysis is performed on each item (indicator) among groups, and the significance analysis of laying rate is as follows:

Statistics of 0.5% Group

| Groups | N | Mean | Standard Deviation | Standard Deviation of Mean |
|---|---|---|---|---|
| Control group | 6 | 91.600 | 3.4774 | 1.4196 |
| 0.5% Group | 6 | 87.617 | 4.4441 | 1.8143 |

| Independent sample test in 0.5% Group | | | | | | | | |
|---|---|---|---|---|---|---|---|---|
| | Levene test of Variance Equation | | T-test of Mean Variance | | | | | |
| | | | | | | Mean | standard error | The 95% confidence interval for the difference | |
| | F | Sig. | t | df | P | difference | difference | lower limit | upper limit |
| Assume that the variances are equal | 1.024 | 0.336 | 1.729 | 10 | 0.114 | 3.9833 | 2.3037 | −1.1496 | 9.1163 |
| Assume that the variances are not equal | | | 1.729 | 9.453 | 0.116 | 3.9833 | 2.3037 | −1.1901 | 9.1568 |

| Statistics of 1.0% Group | | | | |
|---|---|---|---|---|
| Groups | N | Mean | Standard Deviation | Standard Deviation of Mean |
| Control | 6 | 91.600 | 3.4774 | 1.4196 |
| 1.0% Group | 6 | 95.600 | 1.8580 | .7585 |

| Independent sample test in 1.0% Group | | | | | | | | |
|---|---|---|---|---|---|---|---|---|
| | Levene test of Variance Equation | | T-test of Mean Variance | | | | | |
| | | | | | | Mean | standard error | The 95% confidence interval for the difference | |
| | F | Sig. | t | df | P | difference | difference | lower limit | upper limit |
| Assume that the variances are equal | 4.355 | 0.063 | −2.485 | 10 | 0.032 | −4.0000 | 1.6096 | −7.5863 | −.4137 |
| Assume that the variances are not equal | | | −2.485 | 7.640 | 0.039 | −4.0000 | 1.6096 | −7.7423 | −.2577 |

| Statistics of 1.5% Group | | | | |
|---|---|---|---|---|
| Groups | N | Mean | Standard Deviation | Standard Deviation of Mean |
| Control | 6 | 91.600 | 3.4774 | 1.4196 |
| 1.5% Group | 6 | 93.500 | 2.1392 | .8733 |

| | Independent sample test in 1.5% Group | | | | | | | |
|---|---|---|---|---|---|---|---|---|
| | Levene test of Variance Equation | | T-test of Mean Variance | | | | | |
| | | | | | | Mean | standard | The 95% confidence interval for the difference |
| | F | Sig. | t | df | P | difference | error difference | lower limit upper limit |
| Assume that the variances are equal | 2.938 | 0.117 | −1.140 | 10 | 0.281 | −1.9000 | 1.6667 | −5.6137 1.8137 |
| Assume that the variances are not equal | | | −1.140 | 8.310 | 0.286 | −1.9000 | 1.6667 | −5.7187 1.9187 |

From the significance analysis, it can be seen that the laying rate of the 0.5% group and the 1.5% group on day 25 is not significantly different from the control group (P>0.05), but the 1.0% group may significantly increase the egg laying rate (P<0.05), indicating that feeding a specific amount of the *Schizochytrium limacinum* powder 1 may increase the laying rate of laying hens.

When the laying hens are fed the *Schizochytrium limacinum* powder 1, as for the DHA content on the day 15, compared with the control group, in the 0.5% group, it could increase 317.71% to 150 mg/100 g. In the 1.0% group, it could increase 579.48% to 244 mg/100 g. In the 1.5% group, it may increase 885.79% to 354 mg/100 g. After 25 days of feeding, the 0.5% group and 1.0% group remained basically unchanged, while the 1.5% group slightly decreased, but compared with the control group, it still increased significantly. It shows that feeding the *Schizochytrium limacinum* powder 1 may increase the DHA content in laying hen eggs, and the more the addition of the *Schizochytrium limacinum* powder 1 in food, the higher the DHA content in eggs.

When the laying hens are fed the *Schizochytrium limacinum* powder 1, the cholesterol content in eggs decreased significantly. The decrease in the cholesterol content in eggs had no obvious relationship with the content of the *Schizochytrium limacinum* powder 1 in the food, but with the feeding time increases, cholesterol content has a further downward trend. It shows that feeding the *Schizochytrium limacinum* powder 1 may reduce the cholesterol content of laying hen eggs.

According to the above method, when the *Schizochytrium limacinum* powder 1 in the above steps is replaced with the *Schizochytrium limacinum* powder 2, and other steps remain unchanged, the same change trend results are obtained, indicating that both *Schizochytrium limacinum* powder 1 and 2 of Example 1 have the same function.

INDUSTRIAL APPLICATION

The *Schizochytrium limacinum* powder produced by *Schizochytrium limacinum* in the present invention may increase the DHA content in animal products, reduce the cholesterol content in animal products, and also improve the egg production performance of poultry. This animal product with high DHA content from natural sources is organic, safe, stable, and easy to be absorbed. It may be used as a safer and effective way for people to ingest natural DHA, and it may also cater to and meet consumer needs. Thus, *Schizochytrium limacinum* and *Schizochytrium limacinum* powder of the present application have a wide range of application in the field of general food and livestock breeding.

What is claimed is:

1. A method for improving quality and/or increasing a yield of an animal product, including feeding an animal with *Schizochytrium limacinum* or its preparation to improve the quality and/or increase the yield of the animal product; and wherein the *Schizochytrium limacinum* is *Schizochytrium limacinum* HS01 and has a deposit number of CGMCC No. 13746 in the China General Microbiological Culture Collection Center.

2. The method according to claim 1, wherein the improvement of the quality of animal product is c1) and/or c2) and/or c3):
   c1) increase a DHA content in the animal product;
   c2) increase a Sn-2 DHA content in the animal product;
   c3) reduce a cholesterol content in the animal product.

3. The method according to claim 2, wherein the animal is fed with the *Schizochytrium limacinum* preparation having been produced using a method comprising the steps of:
   cultivating the *Schizochytrium limacinum* HS01 to obtain a fermentation broth; and
   using the fermentation broth to produce the *Schizochytrium limacinum* preparation.

4. The method according to claim 3, wherein the culture of the *Schizochytrium limacinum* is carried out using a fermentation medium, which consists of a solvent and solutes, the solvent is water, the solutes and their concentrations are 60-150 g/L of glucose, 8-25 g/L of yeast extract, 3-8 g/L of yeast powder, 5-20 g/L of $Na_2SO_4$, 0.5-1.5 g/L of KCl, 0-3.0 g/L of $MgSO_4$, 0.5-2.5 g/L of $K_2SO_4$, 1.0-2.0 g/L of $KH_2PO_4$, 2.0-5.0 g/L of $(NH_4)_2SO_4$, 0.5-2.5 g/L of $CaCl_2$), 0.001-0.02 g/L of $CuSO_4$, 0.001-0.02 g/L of $ZnSO_4$, 0.001-0.06 g/L of biotin, 0.1-10 g/L of starch and 0-20 g/L of protein powder, respectively, and the pH of the fermentation medium is 4.5-6.5.

5. The method according to claim 3, wherein the preparation is a *Schizochytrium limacinum* powder.

6. The method according to claim 3, wherein producing the preparation by using the fermentation broth includes drying the fermentation broth to obtain the preparation.

7. The method according to claim 3, wherein producing the preparation by using the fermentation broth includes adding an antioxidant to the fermentation broth after obtaining the fermentation broth and then drying to obtain the preparation.

8. The method according to claim 7, wherein the antioxidant is an oil-soluble antioxidant and/or a water-soluble antioxidant;
   wherein the oil-soluble antioxidant is rosemary, mixed natural tocopherols, polyphenols and/or ascorbyl palmitate; and
   wherein the water-soluble antioxidant is phytic acid, ascorbic acid and/or erythorbic acid.

9. The method according to claim 1, wherein the animal is a1) or a2) or a3) or b1) or b2):
   a1) poultry;
   a2) chicken;
   a3) Beijing white chicken, Hy-Line white chicken, Hy-Line brown chicken or Hy-Line pink chicken;
   b1) ruminant;
   b2) cow; and
   wherein the animal product is an egg or milk.

* * * * *